United States Patent
Crouch

(10) Patent No.: US 6,428,497 B1
(45) Date of Patent: Aug. 6, 2002

(54) THERAPEUTIC TABLE SYSTEM

(76) Inventor: Richard A. Crouch, 423 W. Calle Antonia, Tucson, AZ (US) 85706

(*) Notice: Subject to any disclaimer, the term of this patent is extended or adjusted under 35 U.S.C. 154(b) by 0 days.

(21) Appl. No.: 09/944,018

(22) Filed: Sep. 1, 2001

(51) Int. Cl.[7] .................................................. A61F 5/00
(52) U.S. Cl. ......................... 602/32; 606/242; 128/845; 5/624
(58) Field of Search ................................ 606/240, 241, 606/242, 243, 237; 602/32, 33, 35–39; 128/845–846; 5/613–614, 618, 633, 600, 612, 652, 658, 624, 621; 601/24–26; D24/3; D6/37, 8; A61F 5/00

(56) References Cited

U.S. PATENT DOCUMENTS

| | | |
|---|---|---|
| 1,205,649 A | 11/1916 | Miller |
| 2,693,796 A * | 11/1954 | Warner ........................ 601/98 |
| 3,771,518 A * | 11/1973 | Greissing .................... 606/243 |
| D248,406 S | 7/1978 | Hodge |
| 4,354,485 A | 10/1982 | Safadgo |
| 4,579,109 A | 4/1986 | Lundblad |
| 4,856,497 A * | 8/1989 | Westphal ....................... 5/488 |
| 4,890,604 A | 1/1990 | Nelson |
| 4,995,378 A | 2/1991 | Dyer et al. |
| 5,133,741 A * | 7/1992 | Filho ............................. 5/613 |
| 5,505,691 A * | 4/1996 | Fenkell ....................... 601/116 |
| 6,007,568 A * | 12/1999 | Harrell et al. .............. 128/845 |

* cited by examiner

*Primary Examiner*—Michael A. Brown
*Assistant Examiner*—Quang D Thanh

(57) ABSTRACT

A therapeutic table system for supporting a body of a user above a surface and for applying traction to a spine of a user lying on the therapeutic table system. The therapeutic table system includes a table assembly that includes a tabletop and a plurality of leg members. A support assembly is mounted on an upper surface of the tabletop for supporting a body of a user lying on the tabletop. The support assembly includes a hip support assembly for supporting hips of a user lying on the tabletop. The hip support assembly is positionable between an extended position and a contracted position. A traction assembly is mounted on a lower surface of the tabletop for moving the hip support assembly from the contracted position toward the extended position such that a user lying on the tabletop is placed in traction.

17 Claims, 3 Drawing Sheets

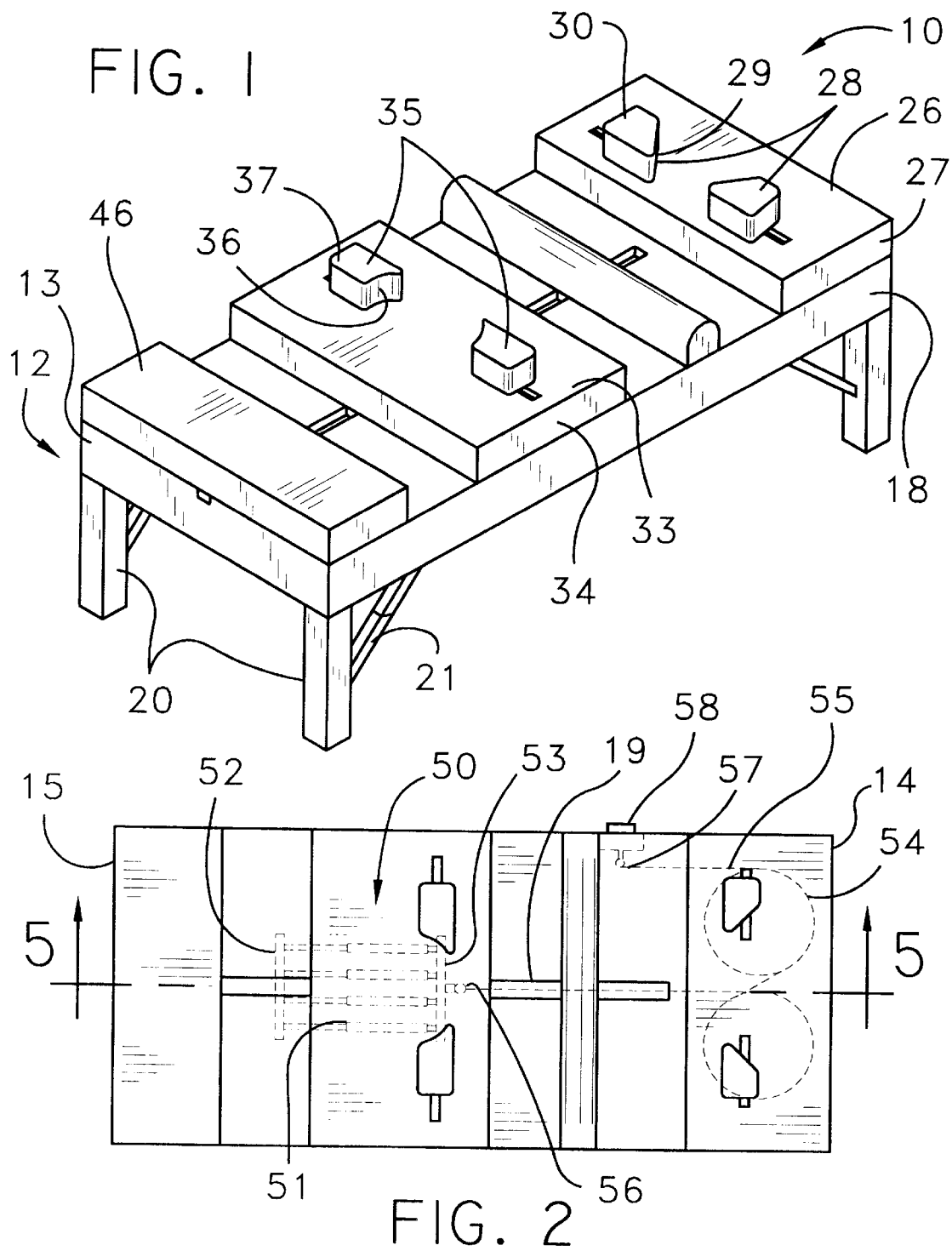

THERAPEUTIC TABLE SYSTEM

BACKGROUND OF THE INVENTION

1. Field of the Invention

The present invention relates to therapeutic tables and more particularly pertains to a new therapeutic table system for supporting a body of a user above a surface and for applying traction to a spine of a user lying on the therapeutic table system.

2. Description of the Prior Art

The use of therapeutic tables is known in the prior art. More specifically, therapeutic tables heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. No. 4,890,604; U.S. Pat. No. 1,205,649; U.S. Pat. No. 4,579,109; U.S. Pat. No. 4,995,378; U.S. Pat. No. 4,354,485; and U.S. Pat. No. Des. 248,406.

While these devices fulfill their respective, particular objectives and requirements, the aforementioned patents do not disclose a new therapeutic table system. The inventive device includes a table assembly that includes a tabletop and a plurality of leg members extending away from the tabletop. A support assembly is mounted on an upper surface of the tabletop for supporting a body of a user lying on the tabletop. The support assembly includes a hip support assembly for supporting hips of a user lying on the tabletop. The hip support assembly is positionable between an extended position and a contracted position. The extended position is characterized by the hip support assembly being positioned generally nearer the second end of the tabletop than the first end of the tabletop. The contracted position is characterized by the hip support assembly being positioned generally nearer the first end of the tabletop than the second end of the tabletop. A traction assembly is mounted on the lower surface of the tabletop for moving the hip support assembly from the contracted position toward the extended position such that a user lying on the tabletop is in traction.

In these respects, the therapeutic table system according to the present invention substantially departs from the conventional concepts and designs of the prior art, and in so doing provides an apparatus primarily developed for the purpose of supporting a body of a user above a surface and for applying traction to a spine of a user lying on the therapeutic table system.

SUMMARY OF THE INVENTION

In view of the foregoing disadvantages inherent in the known types of therapeutic tables now present in the prior art, the present invention provides a new therapeutic table system construction wherein the same can be utilized for supporting a body of a user above a surface and for applying traction to a spine of a user lying on the therapeutic table system.

The general purpose of the present invention, which will be described subsequently in greater detail, is to provide a new therapeutic table system apparatus and method which has many of the advantages of the therapeutic tables mentioned heretofore and many novel features that result in a new therapeutic table system which is not anticipated, rendered obvious, suggested, or even implied by any of the prior art therapeutic tables, either alone or in any combination thereof.

To attain this, the present invention generally comprises a table assembly that includes a tabletop and a plurality of leg members extending away from the tabletop. A support assembly is mounted on an upper surface of the tabletop for supporting a body of a user lying on the tabletop. The support assembly includes a hip support assembly for supporting hips of a user lying on the tabletop. The hip support assembly is positionable between an extended position and a contracted position. The extended position is characterized by the hip support assembly being positioned generally nearer the second end of the tabletop than the first end of the tabletop. The contracted position is characterized by the hip support assembly being positioned generally nearer the first end of the tabletop than the second end of the tabletop. A traction assembly is mounted on the lower surface of the tabletop for moving the hip support assembly from the contracted position toward the extended position such that a user lying on the tabletop is in traction.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new therapeutic table system apparatus and method which has many of the advantages of the therapeutic tables mentioned heretofore and many novel features that result in a new therapeutic table system which is not anticipated, rendered obvious, suggested, or even implied by any of the prior art therapeutic tables, either alone or in any combination thereof.

It is another object of the present invention to provide a new therapeutic table system which may be easily and efficiently manufactured and marketed.

It is a further object of the present invention to provide a new therapeutic table system which is of a durable and reliable construction.

An even further object of the present invention is to provide a new therapeutic table system which is susceptible of a low cost of manufacture with regard to both materials and labor, and which accordingly is then susceptible of low prices of sale to the consuming public, thereby making such therapeutic table system economically available to the buying public.

Still yet another object of the present invention is to provide a new therapeutic table system which provides in the apparatuses and methods of the prior art some of the advantages thereof, while simultaneously overcoming some of the disadvantages normally associated therewith.

Still another object of the present invention is to provide a new therapeutic table system for supporting a body of a user above a surface and for applying traction to a spine of a user lying on the therapeutic table system.

Yet another object of the present invention is to provide a new therapeutic table system which includes a table assembly that includes a tabletop and a plurality of leg members extending away from the tabletop. A support assembly is mounted on an upper surface of the tabletop for supporting a body of a user lying on the tabletop. The support assembly includes a hip support assembly for supporting hips of a user lying on the tabletop. The hip support assembly is positionable between an extended position and a contracted position. The extended position is characterized by the hip support assembly being positioned generally nearer the second end of the tabletop than the first end of the tabletop. The contracted position is characterized by the hip support assembly being positioned generally nearer the first end of the tabletop than the second end of the tabletop. A traction assembly is mounted on the lower surface of the tabletop for moving the hip support assembly from the contracted position toward the extended position such that a user lying on the tabletop is in traction.

Still yet another object of the present invention is to provide a new therapeutic table system that permits a user to solely place their spine and neck in traction. The present invention may be operated by a user using the present invention.

Even still another object of the present invention is to provide a new therapeutic table system that relieves back and neck aches associated with a compressed spine.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a schematic perspective view of a new therapeutic table system according to the present invention.

FIG. 2 is a schematic top view of the present invention.

DESCRIPTION OF THE PREFERRED EMBODIMENT

Figure 3:
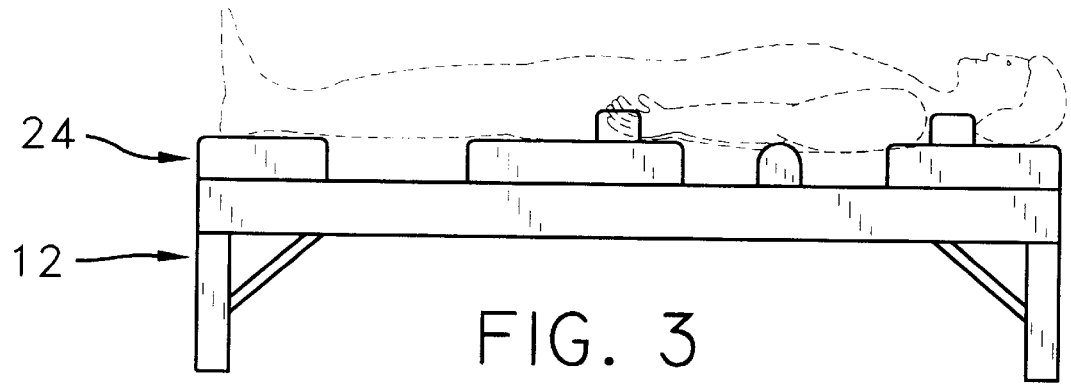
FIG. 3 is a schematic side view of the present invention.
Figure 4:
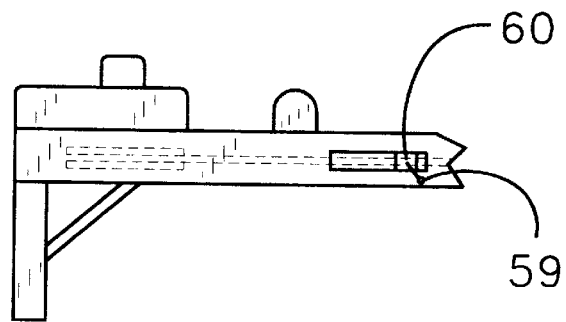
FIG. 4 is a schematic side view of the present invention.

With reference now to the drawings, and in particular to FIGS. 1 through 6 thereof, a new therapeutic table system embodying the principles and concepts of the present invention and generally designated by the reference numeral 10 will be described.

As best illustrated in FIGS. 1 through 6, the therapeutic table system 10 generally comprises a table assembly 12. The table assembly 12 includes a tabletop 13 that has a first end. 14 and a second end 15 opposite the first end 14. The tabletop 13 preferably includes an upper surface 16, a lower surface 17 and a peripheral edge surface 18. The tabletop 13 may also include a longitudinal axis extending between the first 14 and second 15 ends of the tabletop 13.

The tabletop 13 may include an elongated slot 19 extending through the upper 16 and lower 17 surfaces of the tabletop 13. The elongated slot 19 may include a longitudinal axis extending between the first 14 and second 15 ends of the tabletop 13.

A plurality of leg members 20 may be provided for supporting the tabletop 13 above a surface. Each of the leg members 20 may be pivotally mounted to and extending away from the lower surface 17 of the tabletop 13. Each of the leg members 20 may include a support portion 21 for supporting each of the leg members 20 in an extended position with respect to the tabletop 13. Each of the support portions 21 may be mounted to and extending between the plurality of leg members 20 and the lower surface 17 of the tabletop 13. Each of the support portions 21 may also bend allowing each of the leg members 20 to pivot toward the tabletop 13. The table assembly 12 is more easily transportable when each of the leg members 20 is positioned generally adjacent to the tabletop 13.

A support assembly 24 is provided for supporting a body of a user lying on the tabletop 13. The support assembly 24 is preferably mounted on the upper surface 16 of the tabletop 13. The support assembly 24 may include a head support assembly 25 for supporting a neck and head of a user. The head support assembly 25 may be positioned generally adjacent to the first end 14 of the tabletop 13.

The head support assembly 25 may include a base member 26 that has a pair of opposite ends 27 and a longitudinal axis orientated generally perpendicular to the longitudinal axis of the tabletop 13. The head support assembly 25 may also include a pair of head securing members 28 for securing a head of a user in fixed position with respect to the base member 26 of the head assembly 25. Each of the head securing members 28 may be adjustably mounted on the base member 26 of the head support assembly 25. Each of the head securing members 28 may traverse perpendicular to the longitudinal axis of the tabletop.

Each of the head securing members 28 preferably includes a first end 29 and a second end 30. The first ends 29 of each of the securing members may be positioned generally adjacent to each other and each of the head securing members 28 may taper from the second end 30 toward the first end 29 of the securing members 28 for selectively receiving a head of a user lying on the tabletop 13. Each of the securing members 28 and base member 26 may comprise a resiliently compressible material such as, for example, a foam or rubber material.

The support assembly 24 also includes a hip support assembly 32 for supporting hips of a user lying on the tabletop 13. The hip support assembly 32 is preferably adjustably mounted on the tabletop 13. The hip support assembly 32 may include a base member 33 that has a pair of opposite ends 34. The base member 33 includes a protruding portion 42 extending away from the base member 33. The protruding portion 42 of the base member 33 of the hip support assembly 32 is preferably adjustably positioned in the elongated slot 19 of the tabletop 13. The base member 33 of the hip support assembly 32 may include a longitudinal axis orientated generally perpendicular to the longitudinal axis of the tabletop 13. The base member 33 of the hip support assembly 32 may comprise a resiliently compressible material such as, for example, a foam or rubber material.

The hip support assembly 32 also includes a pair of hip securing members 35 for securing hips of a user lying on the tabletop 13 with respect to the base member 33 of the support assembly 32. Each of the hip securing members 35 is preferably adjustably mounted on the base member 33 of the hip support assembly 32. Each of the hip securing members 35 may traverse perpendicular to the longitudinal axis of the tabletop 13.

Each of the hip securing members 35 includes a first end 36 and a second end 37. The first end 36 of each of the hip securing members 35 may be positioned generally adjacent to each other. The first end 36 of each of the hip securing members 35 may be concave for selectively receiving hips of a user lying on the tabletop 13.

The hip support assembly 32 is preferably positionable between an extended position and a contracted position. In one embodiment of the present invention, the extended position is characterized by the hip support assembly 32 being positioned generally nearer the second end 15 of the tabletop 13 than the first end 14 of the tabletop 13. The contracted position is characterized by the hip support assembly 32 being positioned generally nearer the first end 14 of the tabletop 13 than the second end 15 of the tabletop 13.

Each of the hip securing members 35 may comprise a resiliently compressible material such as, for example, a foam or rubber material.

The hip support assembly 32 may also include a plurality of rollers 40 rotatably mounted in the base member 33 of the hip support assembly 32 for more easily moving the hip support assembly 32 between the contracted and extended positions. Each of the rollers 40 selectively abuts the upper surface 16 of the tabletop 13.

Figure 5:
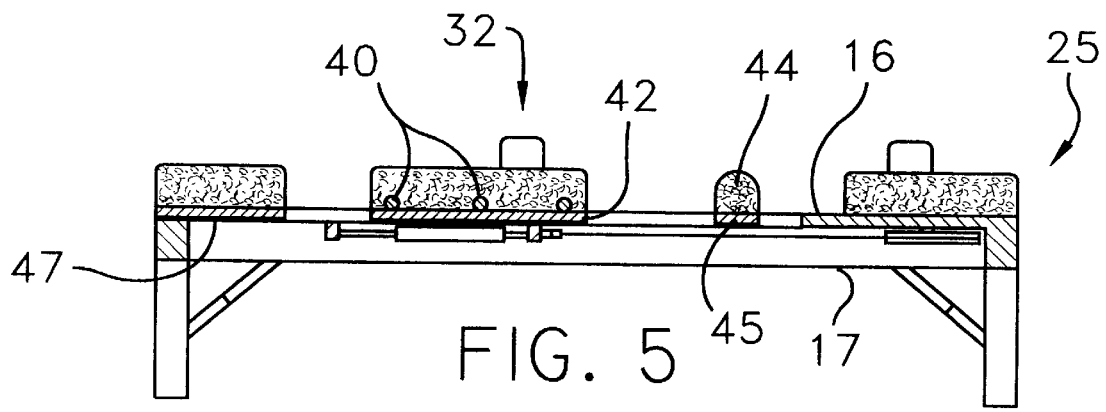
FIG. 5 is a schematic cross-sectional view of the present invention taken along line 5—5 of FIG. 2.

The support assembly 24 may also include a lumbar support member 44 for supporting a lumbar region of a back of a user lying on the tabletop 13. The lumbar support member 44 may be adjustably mounted on the tabletop 13 for adjusting to users of various heights. The lumbar support member 40 may include a protruding portion 45 extending downwardly from a central portion of the lumbar support member 44. In one embodiment of the present invention, as illustrated in FIG. 5, the protruding portion 45 of the lumbar support member 44 is adjustably positioned in the elongated slot 19 in the tabletop 13. The lumbar support member 44 is preferably positioned generally between the hip support assembly 32 and the head support assembly 25.

The lumbar support member 44 may includes a longitudinal axis orientated generally perpendicular to the longitudinal axis of the tabletop 13. The lumbar support member 44 may comprise a resiliently compressible material such as, for example, a foam or rubber material.

The support assembly 24 may also include a feet support member 46 for support feet of a user lying on the tabletop 13. The feet support member 46 may be adjustably mounted on the tabletop 13. The feet support member 46 may include a protruding portion 47 extending downwardly from a central portion of the feet support member 46. The protruding portion 47 of the feet support member 46 may be adjustably positioned in the elongated slot 19 in the tabletop 13. The feet support member 46 may be positioned generally adjacent to the second end 15 of the tabletop 13.

The feet support member 46 may include a longitudinal axis orientated generally perpendicular to the longitudinal axis of the tabletop 13. The feet support member 46 may comprise a resiliently compressible material such as, for example, a foam or rubber material.

A traction assembly 50 is provided for moving the hip support assembly 32 from the contracted position toward the extended position such that a user lying on the tabletop 13 is placed in traction. As illustrated in FIGS. 2 and 5, the traction assembly 50 may be mounted on the lower surface 17 of the tabletop 13.

The traction assembly 50 may include an actuating means 51 for moving the hip support assembly 32 from the contracted position toward the extended position. The actuating means 51 may include a first end 52 and a second end 53. The first end 52 of the actuating means 51 may be mounted on the lower surface 17 of the tabletop 13 and the second end 53 of the actuating means may be mounted on the protruding portion 42 of the base member 33 of the hip support assembly 32.

The actuating means 51 may include an expanded position and a compressed position. In one embodiment of the present invention, the expanded position of the actuating means 51 is characterized by the hip support assembly 32 being in the contracted position such that a user lying on the tabletop 13 is not in traction. The compressed position of the actuating means 51 is characterized by the hip support assembly 32 moving from the contracted position toward the extended position putting a user lying on the tabletop in traction.

The actuating means 51 is preferably in the compressed position in its resting state until placed into the expanded position by a user. The actuating means 51 preferably has the characteristic of automatically moving from the expanded position toward the compressed position. The actuating means 51 may comprise a plurality of contracting plungers. However, the actuating means 51 may comprise any device capable of moving the hip support assembly 32 from the contracted position toward the extended position such as, for example, at least one rubber band.

At least one pulley 54 may be rotatably mounted on the lower surface 17 of the tabletop 13 for moving the actuating means 51 from the compressed position toward the expanded position. The pulley 54 may be positioned generally adjacent to the first end 14 of the tabletop 13. A plurality of pulleys may be employed to more easily move the actuating means 51 from the compressed position toward the expanded position.

A coupling means 55 may be provided for coupling the actuating means 51 and the pulley 54. The coupling means 55 may include a first end 56 and a second end 57. The first end 56 of the coupling means 55 may be mounted on the second end 53 of the actuating means 51. The second end 57 of the coupling means 55 may be positioned generally adjacent to one of the peripheral edge surfaces 18 of the tabletop 13. In one embodiment of the present invention, a portion of the coupling means 55 is positioned about the pulley 54. The coupling means may comprise a cord or a chain, however, other types of coupling means known in the prior art may be employed.

A switch 58 may be provided for moving the actuating means 51 between the expanded and compressed positions. As illustrated in FIG. 2, the switch 58 may be adjustably mounted on one of the peripheral edge surfaces 18 of the tabletop 13. The second end 57 of the coupling means 55 may be mounted on the switch 58.

The switch 58 may include a first position and a second position. In one embodiment of the present invention, the first position is characterized by the actuating means 51 being in the expanded position. The second position of the switch 58 is characterized by the actuating means 51 being in the compressed position.

A securing means 59 may be provided for selectively securing the switch 58 in first position. The securing means 59 may be pivotally mounted on the peripheral edge surface 18 of the tabletop 13 and may be positioned generally adjacent to the switch 58 when the switch 58 is in the first position. An end 60 of the switch 58 may selectively engage a portion of the securing means 59 to secure the switch 58 in the first position. In one embodiment of the present invention, a user disengaging the securing means from the switch moves the actuating means from the expanded position toward the compressed position. The securing means 59 may comprise a hook.

Figure 6:
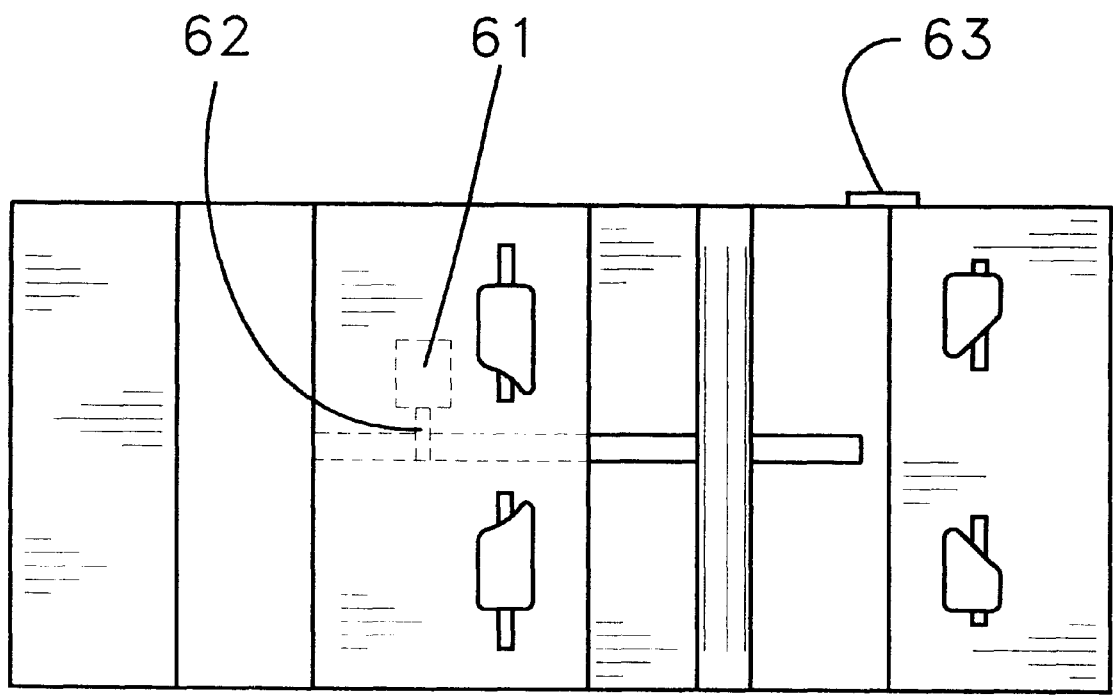
FIG. 6 is a schematic top view of an alternate embodiment of the present invention.

In one embodiment of the present invention, as particularly illustrated in FIG. 6, a motor 61 may be provided for moving the hip support assembly 32 between the contracted and extended positions. The motor 61 may be mounted on the lower surface 17 of the tabletop 13. The motor 61 may include a motor shaft 62 designed for rotational movement. The motor shaft 62 is preferably coupled to the protruding portion 42 of the base member 33 of the hip support assembly 32 such that rotational movement of the motor shaft 62 moves the hip support assembly.

A control means 63 may be provided for controlling the motor 61. The control means 63 may be mounted on the peripheral edge surface 18 of the tabletop such that a user lying on the tabletop 13 may control the motor 61. The control means 63 may also be positioned on a ground or floor surface such that it may be operated by a foot of a person standing next to the tabletop 13.

In use, a user lies on the tabletop 13. The head 28 and hip 35 securing members are positioned such that they selectively abut the neck and hip of the user. The user then releases the securing means 59 causing the switch 58 to move from the first position toward the second position. As the switch 58 moves from the first toward the second position, the actuating means 51 moves from the expanded position toward the compressed position.

The movement of the actuating means 51 from the expanded position toward the compressed position moves the hip support assembly 32 from the contracted position toward the extended position. The movement of the hip support assembly 32 from the contracted to extended positions places the hip support assembly 32 moves from the contracted position toward the extended position it places a back and neck of user lying on the tabletop in traction.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A therapeutic table system for supporting a body of a user above a surface and for applying traction to a spine of a user, said system comprising:

a table assembly including a tabletop having a first end and a second end, said tabletop having an upper surface, a lower surface, and a peripheral edge surface, said tabletop including an elongated slot extending through said upper and lower surfaces of said tabletop and being oriented substantially parallel to a longitudinal axis of said tabletop, said table assembly including a plurality of leg members for supporting said tabletop above a surface;

a support assembly for supporting a body of a user lying on said tabletop, said support assembly being mounted on said upper surface of said tabletop, said support assembly including:

a hip support assembly for supporting hips of a user lying on said tabletop, said hip support assembly being adjustably mounted on said tabletop, a portion of said hip support assembly extending into said slot of said tabletop and being adjustably positionable along said elongated slot;

said hip support assembly being positionable between an extended position and a contracted position, wherein said extended position is characterized by said hip support assembly being positioned generally nearer said second end of said tabletop than said first end of said tabletop, wherein said contracted position is characterized by said hip support assembly being positioned generally nearer said first end of said tabletop than said second end of said tabletop;

a traction assembly for moving said hip support assembly from said contracted position toward said extended position, said traction assembly being mounted on said lower surface of said tabletop; and a feet support member for supporting feet of a user lying on said tabletop, said feet support member being movable mounted on said tabletop, said feet support member including a feet protruding portion extending away from said feet support member, said feet protruding portion of said feet support member being adjustably movable along said elongated slot in said tabletop.

2. The therapeutic table system of claim 1, wherein each of said leg members is pivotally mounted to and extending away from said lower surface of said tabletop.

3. The therapeutic table system of claim 2, wherein each of said leg members includes a support portion for bracing said leg member each of said support portions being mounted to and extending between one of said plurality of leg members and said lower surface of said tabletop.

4. The therapeutic table system of claim 1, wherein said support assembly additionally includes a head support assembly for supporting a neck and head of a user, said head support assembly including:
    a head base member having a pair of opposite ends; and
    a pair of adjustable head securing members for securing a head of a user in a fixed position with respect to said head base member of said head support assembly.

5. The therapeutic table system of claim 4, wherein each of said head securing members is adjustably mounted on said head base member of said head support assembly, each of said head securing members being movable in a direction extending substantially perpendicular to the longitudinal axis of said tabletop.

6. The therapeutic table system of claim 4, wherein each of said head securing members includes a first end and a second end, said first ends of said head securing members being positioned generally adjacent to each other, each of said head securing members being tapered in width from said second end toward said first end of said securing members.

7. A therapeutic table system for supporting a body of a user above a surface and for applying traction to a spine of a user, said system comprising:
    a table assembly including a tabletop having a first end and a second end, said tabletop having an upper surface, a lower surface, and a parallel edge surface, said tabletop including said elongated slot extending through said upper and lower surfaces of said tabletop and being oriented substantially perpendicular to a longitudinal axis of said tabletop, said table assembly including a plurality of leg members for supporting said tabletop above a surface;
    a support assembly for supporting a body of a user lying on said tabletop, said support assembly being mounted on an upper surface of said tabletop, said support assembly including:
        a hip support assembly for supporting hips of a user lying on said tabletop, said hip support assembly being adjustably mounted on said tabletop, a portion of said hip support assembly extending into said slot of said tabletop and being adjustably positionable along said elongated slot; and
        said hip support assembly being positionable between an extended position and a contracted position, wherein said extended position is characterized by said hip support assembly being positioned generally nearer said second end of said tabletop than said first end of said tabletop, wherein said contracted position is characterized by said hip support assembly being positioned generally nearer said first end of said tabletop than said second end of said tabletop;
    a traction assembly for moving said hip support assembly from said contracted position toward said extended position, said traction assembly being mounted on said lower surface of said tabletop;
    a hip base member being adjustably mounted on said tabletop, said hip base member having a hip protruding portion extending away from said hip base member, said hip protruding portion being positioned in said elongated slot in said tabletop; and
    a pair of hip securing members for securing hips of a user lying on said tabletop with respect to said hip base member of said support assembly, each of said hip securing members being adjustably mounted on said hip base member of said hip support assembly, each of said hip securing members being movable in a direction extending substantially perpendicular to the longitudinal axis of said tabletop.

8. The therapeutic table system of claim 7, wherein each of said hip securing members includes a first end and a second end, said first ends of said hip securing members being positioned generally adjacent to each other, said first end of each of said hip securing members being concave for receiving hips of a user lying on said tabletop.

9. The therapeutic table system of claim 1, additionally including a lumbar support member for supporting a lumbar region of a back of a user lying on said tabletop, said lumbar support being adjustably mounted on said tabletop, said lumbar support member having a lumbar protruding portion extending downwardly from a central portion of said lumbar support member, wherein said lumbar protruding portion is adjustably movable along said elongated slot in said tabletop.

10. A therapeutic table system for supporting a body of a user above a surface and for applying traction to a spine of a user, said system comprising:
    a table assembly including a tabletop having a first end and a second end, said tabletop having an upper surface, a lower surface, and a parallel edge surface, said tabletop including an elongated slot extending through said upper and lower surfaces of said tabletop and being oriented substantially perpendicular to a longitudinal axis of said tabletop, said table assembly including a plurality of leg members for supporting said tabletop above a surface;
    a support assembly for supporting a body of a user lying on said tabletop, said support assembly being mounted on and upper surface of said tabletop, said support assembly including:
        a hip support assembly for supporting hips of a user lying on said tabletop, said hip support assembly being adjustably mounted on said tabletop, a portion of said hip support assembly extending into said slot of said tabletop and being adjustably positionable along said elongated slot; and
        said hip support assembly being positionable between an extended position and a contracted position, wherein said extended position is characterized by said hip support assembly being positioned generally nearer said second end of said tabletop than said first end of said tabletop, wherein said contracted position is characterized by said hip support assembly being positioned generally nearer said first end of said tabletop than said second end of said tabletop; and
    a traction assembly for moving said hip support assembly from said contracted position toward said extended position, said traction assembly being mounted on said lower surface of said tabletop;
    a hip base member being adjustably mounted on said tabletop said hip base member having a hip protruding portion extending away from said hip base member, said hip protruding portion being positioned in said elongated slot in said tabletop;
    a pair of hip securing members for securing hips of a user lying on said tabletop with respect to said hip base member of said support assembly, each of said hip securing members being adjustably mounted on said hip base member of said hip support assembly, each of said hip securing members being movable in a direction extending substantially perpendicular to the longitudinal axis of said tabletop;
    said traction assembly including an actuating means for moving said hip support assembly from said contracted position toward said extended position, said actuating means having a first end and a second end, said first end being mounted on a lower surface of said tabletop, said second end being mounted on said hip protruding portion of said hip base member of said hip support assembly; and said actuating means having an expanded position and a compressed position, wherein said expanded position of said actuating means is characterized by said hip support assembly being in said contracted position such that traction is not applied to a user lying on said tabletop, wherein said compressed position of said actuating means is characterized by said hip support assembly moving from said contracted position toward said extended position to apply traction to a user lying on said tabletop.

11. The therapeutic table system of claim 10, wherein said actuating means comprises a plurality of contracting plungers.

12. The therapeutic table system of claim 10, additionally including:

a pair of pulleys being rotatably mounted on said lower surface of said tabletop; and a coupling means for coupling said actuating means and each of said pulleys, said coupling means having a first end and a second end, said first end of said coupling means being mounted on said second end of said actuating means, said second end of said coupling means being positioned generally adjacent to said peripheral edge surface of said tabletop, wherein a portion of said coupling means being positioned about each of said pulleys.

13. The therapeutic table system of claim 12, wherein said coupling means comprises a cord.

14. The therapeutic table system of claim 12, additionally including a switch for causing movement of said actuating means between said expanded and compressed positions.

15. The therapeutic table system of claim 14, wherein said switch is mounted on said peripheral edge surface of said tabletop, said second end of said coupling means being mounted on said switch;

said switch having a first position and a second position, wherein said first position is characterized by said actuating means being in said expanded position, wherein said second position of said switch is characterized by said actuating means being in said compressed position; and a securing means for selectively securing said switch in said first position, said securing means being pivotally mounted on said peripheral edge surface of said tabletop, an end of said switch selectively engaging a portion of said securing means.

16. The therapeutic table system of claim 7, additionally including a motor for moving said hip support assembly between said contracted and extended positions;

said motor including a motor shaft adapted for rotational movement, said motor shaft being coupled to said protruding portion of said base member of said hip support assembly; and a control means for controlling said motor, said control means being mounted on said tabletop and electrically connected to said motor.

17. The therapeutic table system of claim 7, additionally including a plurality of rollers rotatably mounted in the base member of the hip support assembly for facilitating movement of said hip support assembly between the contracted and extended positions, each of said rollers selectively abutting an upper surface of the tabletop.

* * * * *